US 10,576,172 B2
Mar. 3, 2020

(12) United States Patent
Bashirullah

(54) POWERING AN IN VIVO DEVICE USING ENERGY FROM A RADIOACTIVE SOURCE

(71) Applicant: Galvani Bioelectronics Limited, Brentford, Middlesex (GB)

(72) Inventor: Rizwan Bashirullah, Gainesville, FL (US)

(73) Assignee: GALVANI BIOELECTRONICS LIMITED, Brentford (GB)

( * ) Notice: Subject to any disclaimer, the term of this patent is extended or adjusted under 35 U.S.C. 154(b) by 0 days.

(21) Appl. No.: 15/803,496

(22) Filed: Nov. 3, 2017

(65) Prior Publication Data
US 2018/0126015 A1    May 10, 2018

Related U.S. Application Data

(60) Provisional application No. 62/417,426, filed on Nov. 4, 2016.

(51) Int. Cl.
*A61K 51/12* (2006.01)
*G21H 1/02* (2006.01)
*H02H 9/00* (2006.01)

(52) U.S. Cl.
CPC .......... *A61K 51/1282* (2013.01); *G21H 1/02* (2013.01); *H02H 9/002* (2013.01)

(58) Field of Classification Search
CPC .............................. H02J 7/025; A61K 51/1282
USPC ......................................................... 320/108
See application file for complete search history.

(56) References Cited

U.S. PATENT DOCUMENTS

| 4,015,609 A * | 4/1977 | Mensink ................. A61N 1/378 323/911 |
| 5,082,505 A | 1/1992 | Cota et al. |
| 7,621,878 B2 * | 11/2009 | Ericson ................ A61B 5/0031 128/903 |
| 9,224,901 B1 * | 12/2015 | Squillante ................ G21H 1/12 |
| 2015/0080982 A1 * | 3/2015 | Van Funderburk .......................... A61N 1/37217 607/59 |

OTHER PUBLICATIONS

International Patent Application No. PCT/US2017/059936; Int'l Written Opinion and the Search Report; dated Jan. 29, 2018; 8 pages.

(Continued)

*Primary Examiner* — Edward Tso
*Assistant Examiner* — Ahmed H Omar
(74) *Attorney, Agent, or Firm* — BakerHostetler

(57) ABSTRACT

An implantable system is disclosed that includes an encapsulated housing including a radioactive source. The encapsulated housing is internally coated with a light-generating coating that converts the radioactive energy to light, that is then output in vivo to a photodiode positioned proximate to at least part of the encapsulated housing in vivo. The photodiode is configured to generate electrical current from the light, which electrical current is output to a power conditioning circuit that is configured to use the electrical current as an input electrical current and to output power to a load in vivo. The encapsulated may also be internally coated, at least in part, with a light directing coating that causes light to be directed toward an optical lens that focuses the light on the photodiode. The radioactive source may be a gas having a low half-life and which poses no health risk to a patient if released.

11 Claims, 3 Drawing Sheets

(56) References Cited

OTHER PUBLICATIONS

International Patent Application No. PCT/US2017/059936; Int'l Preliminary Report on Patentability; dated May 16, 2019; 8 pages.

* cited by examiner

POWERING AN IN VIVO DEVICE USING ENERGY FROM A RADIOACTIVE SOURCE

CROSS REFERENCE TO RELATED APPLICATIONS

This application benefits from the priority of U.S. Application No. 62/417,426, filed Nov. 4, 2016, and entitled "Powering an In Vivo Device Using Energy from a Radioactive Source" the disclosure of which is incorporated herein by its entirety

TECHNICAL FIELD

The present disclosure relates to in vivo implantable devices, and more particularly, though not necessarily exclusively, to systems for generating power using energy from a radioactive source in vivo.

BACKGROUND

An in vivo implantable device can include a power source, such as a battery, that is rechargeable. The battery can be recharged by wirelessly transferring power from a device positioned ex vivo. Recharging the battery often involves good patient compliance—e.g., by the patient operating the ex vivo device on a set schedule or by the patient visiting a medical professional frequently. Frequently recharging implantable device batteries can be burdensome and failure to recharge the battery frequently can result in inadequate treatment.

DETAILED DESCRIPTION

Figure 1:
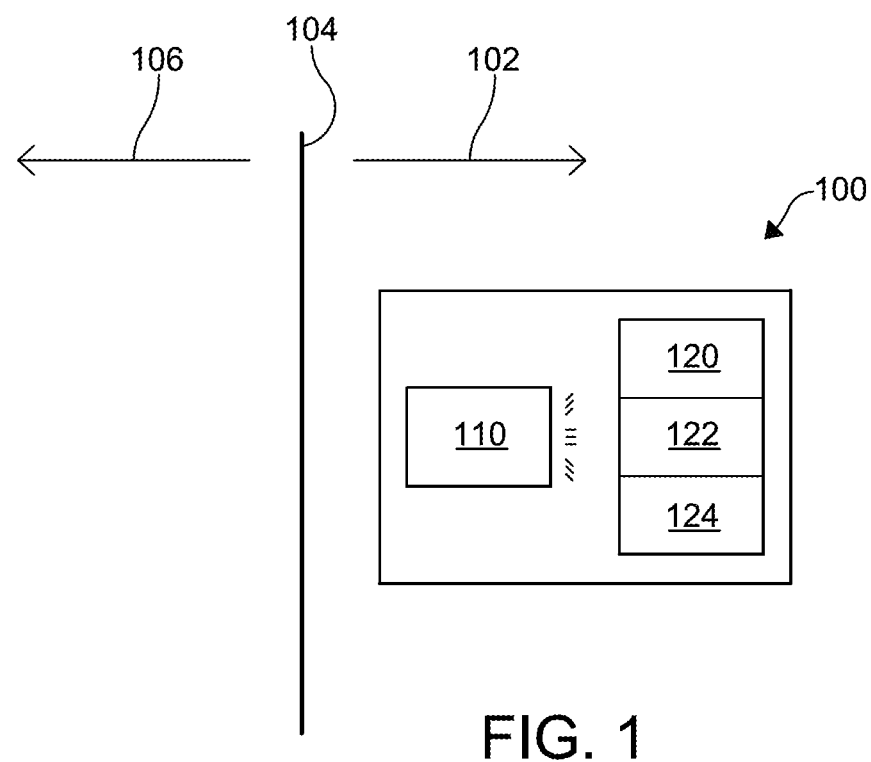
FIG. 1 is a block diagram an implantable device powered at least in part from light generated based on energy from a radioactive source according to one example of the present disclosure.

Certain aspects and features relate to generating electrical current in vivo from light that is generated based on energy from a radioactive source in vivo. The generated electrical current can be used to power a load of an implantable device, such as by recharging a power source included with the implantable device or by delivering power directly to the load. In some examples, an encapsulated housing for a radioactive source includes a coating that responds to energy—e.g., in the form of electrons—from the radioactive source by generating light. A photodetector can be positioned with respect to the encapsulated housing and generate electrical current from the light. A power conditioning circuit can use the electrical current to provide output power to a load in vivo. By using energy from a radioactive source in vivo, a power source for an implantable device can be recharged from an ex vivo power source less frequently or not at all and continue to provide treatment or monitoring services. By using a photodetector to convert light to electrical current, the radioactive source can be safely contained within an encapsulated housing and does not need to connect physically to other devices to transfer energy via light.

In one example, an implantable power source can extract energy from a radioactive source emitting beta particles (electrons), which are captured by a phosphorescent layer and transformed into light, by transforming the received light into electricity using a photodetector, such as a photodetector using a semiconducting photodiode. The radioactive material can be in an encapsulated housing that is hermetically sealed, such as a glass vessel, of any form or shape. An example of the radioactive source is tritium gas that can be a low-radiation beta emitter. The inner walls of the glass vessel can be coated with a layer of phosphorescent powder, such as zinc sulfide, that can respond to electrical energy from the radioactive source by outputting light.

Tritium gas includes atoms with two neutrons and one proton, similar to hydrogen. When tritium decays, electrons with a half-life of roughly 12.3 years are emitted. The phosphorescent layer inside the glass vessel or capsule can respond to the emitted electrons by transforming the energy into light. The wavelength of the light (or its color) can depend on the glass coating rather than the tritium gas inside the vessel. By varying the glass coating, the color of the light from the encapsulated housing can be varied. The brightness of the color generated from the encapsulated housing can be controlled by adjusting the filling pressure or quantity of the gas inside the vessel, as brightness can be proportional to the pressure.

Photons from the encapsulated housing can be converted into electricity using a photodetector that is positioned proximate to at least part of the encapsulated housing. The photodetector can generate an electrical current when sufficiently energetic photons create electron-hole pairs (EHP) by exciting electrons from the valence band to the conduction band of a semiconductor with bandgap "Eg," and any photon energy in excess of the semiconductor bandgap Eg is lost as lattice vibrations, or phonons.

A radioactive source according to some examples can be included in an encapsulated housing, hermetically sealed, for example using laser welding encapsulation processes. The encapsulated housing can have a very small form factor to facilitate its implantation as part of the implantable device in vivo. The radioactive source can be in a gaseous state, and the encapsulated housing can be considered safe as the energy that is emitted during radioactive decay in the case of tritium is a maximum of approximately 18 keV, which is low compared to other radioactive isotopes. This weak emission cannot penetrate a thin sheet of paper or travel more than five mm in air, and is therefore safely sealed within a glass, ceramic, or similar capsule. Even if the glass seal breaks, the amount of tritium that would be absorbed or inhaled can be comparable to exposure to natural atmospheric radiation.

Energy conversion efficiency can be improved by selecting the relative spectral response (or sensitivity to light of a certain wavelength or color) of the photodetector so that it matches the relative spectral output of the encapsulated housing. The spectral response of the photodetector can be set by the semiconducting material used to manufacture the photodetector. The spectral output of the encapsulated housing can be controlled by the phosphorescent coating. An optical lens positioned between the photodetector and the encapsulated housing can further improve the conversion efficiency by focusing the photon flux from the encapsulated housing on the desired active area of the photodiode. In some examples, a reflector can be used to collect and direct the light towards the photodetector to improve conversion efficiency. In further examples, the sides (or portions), except for one, of the encapsulated housing can be coated with a material to focus the light to the one side of the encapsulated housing and the photodetector can be positioned proximate to that side (or portion). In still further examples, the encapsulated housing can have a coating on an inner wall that responds to energy from the radioactive source by outputting light, and the wavelength of the light can be controlled by the type of coating used, or by adding additional coatings to the inner wall or the outer wall of the encapsulated housing. The wavelength may be selected based on the wavelength of light at which the photodetector efficiently transforms light to electrical current.

Although for patient safety and other reasons, the amount of irradiance or light intensity from the encapsulated housing may be relatively low, the radioactive source can generally be expected to last for at least the half-life of the radioactive source. In the case of tritium, that is approximately 12.3 years. Since the low irradiance of the radioactive source can cause the photodetector to produce a proportionally small electrical current, various aspects of the implantable device power system can be used as a trickle-charging circuit. In one embodiment, the photodetector can supply a relatively small electrical current, perhaps too small to power a load on its own, but does so at a constant rate sufficient to constantly recharge a secondary battery or other rechargeable power source of the implantable device. For example, the power conditioning circuit can use the electrical current from the photodetector to recharge a secondary battery, by conditioning the current and voltage supplied to trickle charge the battery.

A power conditioning circuit according to some examples can bias the photodetector in a photoconductive mode to charge a storage capacitor continuously. The storage capacitor can be sampled periodically by moving the charge stored in the capacitor to the battery using a switched capacitor voltage converter. Alternatively, the capacitor can be sampled when the voltage across it reaches a predetermined voltage value. The battery can also supply power and the photodetector can supply sufficient electrical current to the power conditioning circuit to overcome the standby power losses and the self-discharge of the battery to be effective. Extremely low power and efficient circuits and high-quality factor capacitors and switches can be used to minimize the power dissipated within the circuits.

Using a radioactive power source and system in vivo according to some examples can result in an implantable device that requires no or infrequent recharging by ex vivo power sources. In some examples, an implantable device suitable as an implantable medical device in neuromodulation systems can be self-sufficient or near self-sufficient for an extended period, such as over ten years. Neuromodulation systems that require infrequent stimulation of the nerves, and hence small average power, may be supplied power directly from electrical current generated by the photodetector. In such a system, an initial charge can be supplied wirelessly by an ex vivo charger, using for example, an inductive power resonant link, rectifier, and regulator, to power-up the system.

Detailed descriptions of certain examples are discussed below. These illustrative examples are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative examples but, like the illustrative examples, should not be used to limit the present disclosure. The various figures described below depict examples of implementations for the present disclosure, but the figures should not be used to limit the present disclosure.

FIG. 1 is a block diagram an implantable device 100 powered at least in part from light generated based on energy from a radioactive source according to one example of the present disclosure. The implantable device 100 is positioned on the in vivo side 102 of body tissue 104, with no coupling device on the ex vivo side 106. The implantable device 100 includes an encapsulated housing 110, a photodetector 120, a power conditioning circuit 122, and a load 124. The implantable device 100 can include a biocompatible housing in which these components are located. In other examples, some, but not all, of the components are included within the implantable device housing.

The encapsulated housing 110 may be glass or made from other relatively light-transparent material. In the encapsulated housing 110 are a radioactive source and a coating that can respond to energy from the radioactive source by generating light. The radioactive source may be in a gaseous state to facilitate a small form factor for the encapsulated housing.

The photodetector 120 can detect light generated by the coating and generate electrical current based on the light. The power conditioning circuit 122 can manage the electrical current—such as by smoothing and regulating the electrical current—to generate output power for the load 124.

Figures 2, 3:
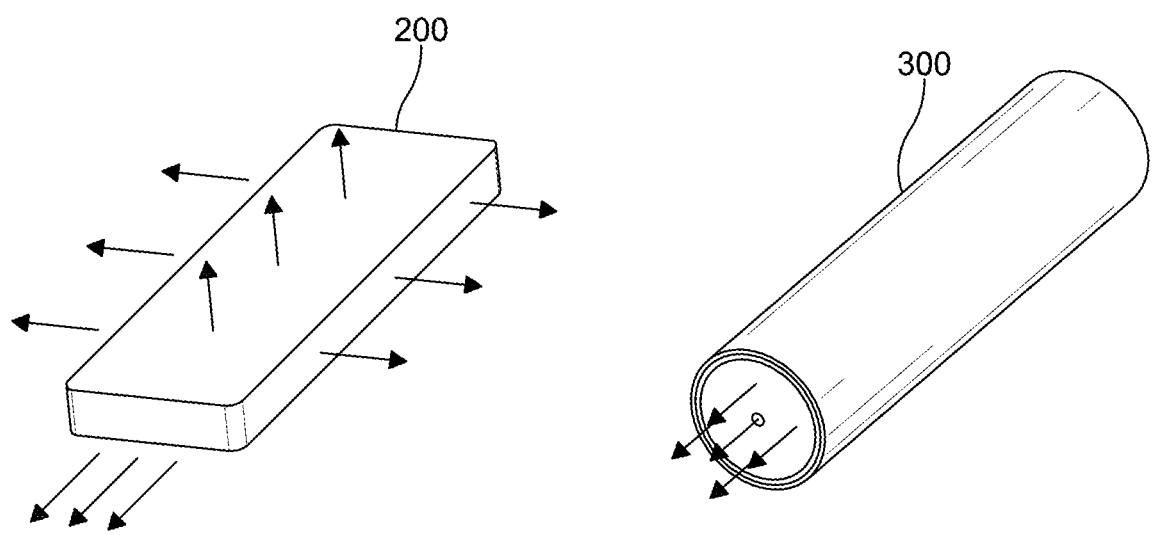
FIG. 2 is a perspective view of an encapsulated housing for a radioactive source according to one example of the present disclosure.
FIG. 3 is a perspective view of an encapsulated housing for a radioactive source according to another example of the present disclosure.

The encapsulated housing 110 can be any shape and size as needed for a particular application in vivo. FIGS. 2 and 3 show by perspective view two examples of an encapsulated housing 200 and 300, respectively. FIG. 2 depicts a substantially rectangular encapsulated housing 200 and FIG. 3 depicts a substantially oval or oblong encapsulated housing 300. In each case, light is emitted as indicated by the arrows. The encapsulated housings 200 and 300 include a radioactive source, such as tritium in gaseous form, and a coating on at least part of the inner walls of the encapsulated housing. The coating, which may be a phosphorescent coating, can respond to energy from the radioactive source by emitting light.

Figure 4:
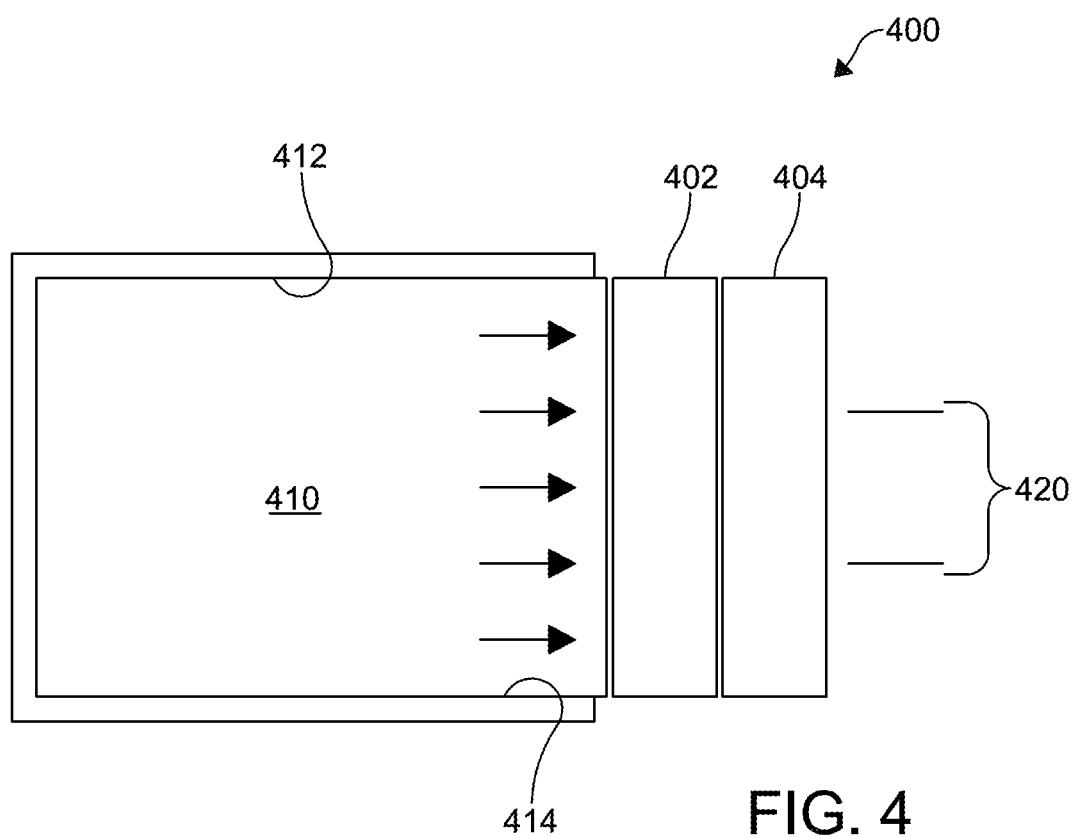
FIG. 4 is a schematic block diagram of part of an implantable device according to one example of the present disclosure.

FIG. 4 is a schematic block diagram of part of an implantable device according to one example of the present disclosure. The implantable device includes an encapsulated housing 400, an optical lens 402, and a photodetector 404, such as a photodiode. The encapsulated housing 400 includes a radioactive source 410 and a light-generating coating 412 on an inner wall of the encapsulated housing 400 that can respond to energy from the radioactive source 410 by generating light, which is shown via arrows in FIG. 4. The encapsulated housing can also have a light-directing coating 414 (or light-directing component) internal or external to part of the encapsulated housing 400. The light-directing coating 414 may be reflective or otherwise configured to direct light toward part of the encapsulated housing 400 to which the photodiode 404 is proximately located so that more of the light energy generated by the encapsulated housing 400 is provided toward the photodiode 404.

The optical lens 402 can be positioned between the encapsulated housing 400 and the photodiode 404. The optical lens 402 can focus light from the encapsulated housing 400 toward the photodiode 404 to improve the efficiency of transferring light energy from the encapsulated housing 400 to the photodiode 404. In other examples, the implantable device does not include an optical lens positioned between the encapsulated housing and the photodiode.

The photodiode 404 can generate an output electrical current 420 in response to the light. The amount of electrical current generated by the photodiode 404 can be proportional to the amount of light detected by the photodiode 404. The amount of light detected by the photodiode 404 depends on the amount of light outputted from the encapsulated housing 400. The amount of light outputted from the encapsulated housing 400 depends on the amount of energy released by the radioactive source 410 in the encapsulated housing 400 and the characteristics of the light-generating coating 412 on the encapsulated housing 400.

Figure 5:
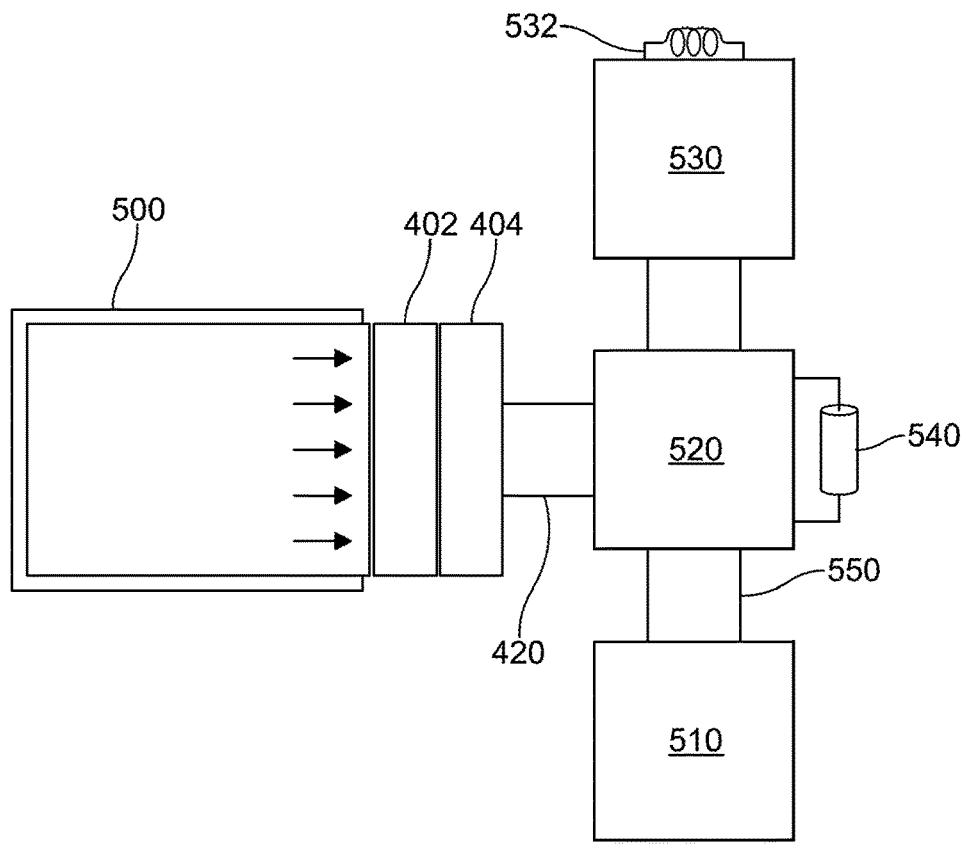
FIG. 5 is a schematic block diagram of an implantable device with a load according to one example of the present disclosure.

The output current 420 can be used to power a load (not shown in FIG. 4) of the implantable device 400, directly after conditioning or indirectly by recharging a power source that is used to provide power for the load. FIG. 5 is a schematic block diagram of an implantable device 500, such as that shown in FIG. 4, with a load 510 according to one example of the present disclosure. The implantable device 500 includes the components of FIG. 4, in addition to a power conditioning circuit 520, a wireless charging interface 530 with a coil 532, a rechargeable power source 540, and the load 510. The load 510 may be an implant subsystem, such as a radio, a processor, or a stimulator, and may represent one or more loads for the implantable device.

The power conditioning circuit 520 can receive the output electrical current 420 from the photodiode 404 as an input electrical current and transform the input electrical current 420 into output power 550 to the load 510 or to the rechargeable battery 540. The power conditioning circuit 520 can also manage providing output power to the load 510 from the rechargeable battery 540. The power conditioning circuit 520 can also manage power received via another device via the wireless charging interface 530 and coil 532 through wireless induction. For example, the power conditioning circuit can transport that power into output power for the load 510 or the rechargeable battery 540 if further recharging is needed or if the radioactive source for power fails or fails to provide sufficient power. In some examples, the wireless charging interface may not be necessary and is not included in the implantable device.

Figure 6:
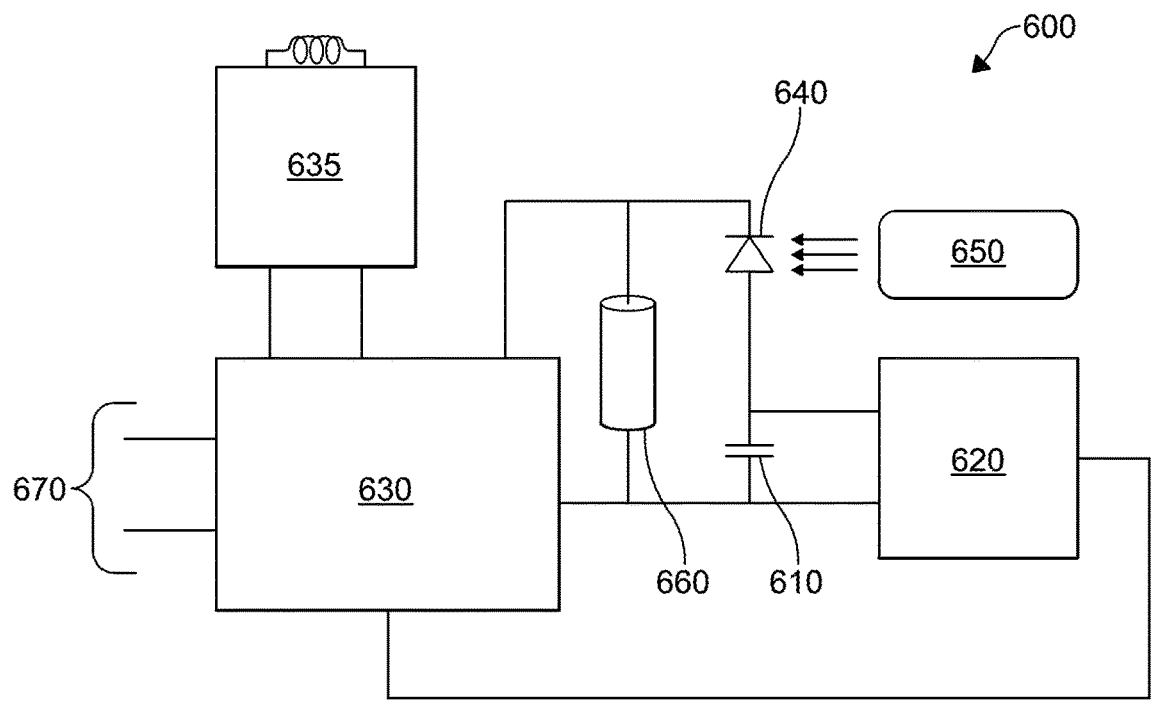
FIG. 6 is a schematic diagram of part of an implantable device according to one example of the present disclosure.

FIG. 6 is a schematic diagram of part of an implantable device according to one example of the present disclosure. The schematic diagram depicts components of a power conditioning circuit 600 according to one example. The power conditioning circuit 600 can include a storage capacitor 610, a voltage converter 620, and a regulator 630 that can provide regulated output power to a load.

A photodetector 640, depicted as a photodiode, can generate electrical current in response to light, shown as arrows, from an encapsulated housing with a radioactive source 650. The electrical current can charge the storage capacitor 610. The voltage converter 620 can periodically receive the charge from the storage capacitor 610 and condition the charge into a direct current (DC) voltage that is supplied to the regulator 630. The regulator 630 can stabilize the DC voltage (and stabilize power received from a wireless charging interface 635) and use it to recharge a rechargeable power source 660, such as a battery, or provide regulated output power 670 for a load.

The photodetector 610 can be biased in either a photovoltaic mode or a photoconductive mode. In the photovoltaic mode, the flow of current from the photodetector 610 can be restricted so a voltage builds up in the photodetector. In the photoconductive mode, the photodetector 610 can be reverse biased, for example by the rechargeable power source or output from the regulator.

Using certain examples of the present disclosure can allow an implantable device to avoid being recharged by an ex vivo device, or at least avoid being recharged by an ex vivo device as frequently as otherwise. In addition, by using light to carry energy from a radioactive source in an encapsulated housing to a load of an implantable device, the implantable device, with the encapsulated housing can have a flexible form factor that can be changed or designed to fit a particular desired application. For example, the photodetector and other components of the implantable device are not required to be within the same housing or structure as the encapsulated housing that includes the radioactive material. And, using light to transfer power from a radioactive source can allow the radioactive source to be safely embedded in the encapsulated housing.

The foregoing description of the examples, including illustrated examples, of the invention has been presented only for the purpose of illustration and description and is not intended to be exhaustive or to limit the invention to the precise forms disclosed. Numerous modifications, adaptations, and uses thereof will be apparent to those skilled in the art without departing from the scope of this invention. The illustrative examples described above are given to introduce the reader to the general subject matter discussed here and are not intended to limit the scope of the disclosed concepts.

What is claimed:

1. An implantable system comprising:
    an encapsulated housing defining a chamber to include a radioactive source, the encapsulated housing being configured to output light in vivo based on energy from the radioactive source;
    a photodiode positioned proximate to at least part of the encapsulated housing in vivo, the photodiode being configured to generate electrical current from the light; and
    a power conditioning circuit configured to use the electrical current as an input electrical current and to output power to a load in vivo;
    wherein the encapsulated housing encases the radioactive source and includes a light-generating coating on an inner wall of the encapsulated housing that responds to energy from the radioactive source by generating light, and a light-directing coating internal or external to part of the encapsulated housing, wherein the light-directing coating is configured to focus generated light toward part of the encapsulated housing to which the photodiode is proximately located so that more of the light energy generated by the encapsulated housing is provided toward the photodiode.

2. The implantable system of claim 1, further comprising:
    an optical lens positioned between the photodiode and the encapsulated housing, wherein the optical lens is configured to focus light from the encapsulated housing toward the photodiode.

3. The implantable system of claim 1, wherein an amount of the power output to the load in vivo is based on the input electrical current.

4. The implantable system of claim 1, further comprising:
    a rechargeable power source that is at least in part rechargeable from the input electrical current.

5. The implantable system of claim 4, further comprising:
a wireless charging interface with at least one coil configured to wirelessly receive power to recharge the power source and provide power to the load.

6. The implantable system of claim 1, wherein the encapsulated housing is a transparent housing that includes the light-directing coating, the light-directing coating being configured to focus light generated in response to the energy from the radioactive source toward the photodiode.

7. The implantable system of claim 1, wherein the power conditioning circuit includes:
a storage capacitor;
a regulator configured to output the power to the load in vivo; and
a voltage converter configured to condition a charge from the storage capacitor for the regulator.

8. The implantable system of claim 1 wherein the radioactive source is tritium, wherein an amount of electrical current generated by the photodiode is configured to be proportional to an amount of light from the encapsulated housing, the amount of light from the encapsulated housing is configured to be proportional to an amount of energy from the radioactive source.

9. The implantable system of claim 1, wherein the 1 light-generating coating is selected such that the encapsulated housing is configured to output light at a wavelength that is selected based on a performance characteristic of the photodiode.

10. An implantable system, comprising:
a photodetector configured to generate an electrical current from light generated based on energy from a radioactive source in vivo, wherein the radioactive source is contained in an encapsulated housing that includes a light-generating coating on an inner wall of the encapsulated housing and a light-directing coating internal or external to part of the encapsulated housing, wherein the light-generated coating responds to energy from the radioactive source by generating light, and wherein the light-directing coating is configured to direct light toward part of the encapsulated housing to which the photodetector is proximately located;
an optical lens positioned in vivo between the radioactive source and the photodetector, wherein the optical lens is configured to focus light from the radioactive source toward the photodetector;
a power conditioning circuit configured to use the electrical current to generate output power; and
a load in vivo configured to use the output power.

11. A method comprising:
generating light in vivo using a radioactive source in vivo;
focusing the light using an optical lens in vivo toward a photodetector;
generating, by the photodetector, electrical current from the light; and
using the electrical current to charge a power source in vivo or output power to a load of an implantable device in vivo;
wherein the radioactive source in contained in an encapsulated housing, wherein the encapsulated housing includes a light-generating coating on an inner wall of the encapsulated housing that responds to energy from the radioactive source by generating light, and a light-directing coating internal or external to part of the encapsulated housing, wherein the light-directing coating is configured to direct light toward part of the encapsulated housing to which the optical lens and photodetector are proximately located.

* * * * *